US 10,617,411 B2

(12) United States Patent
Williams

(10) Patent No.: US 10,617,411 B2
(45) Date of Patent: Apr. 14, 2020

(54) ADAPTER ASSEMBLY FOR SURGICAL DEVICE

(71) Applicant: Covidien LP, Mansfield, MA (US)

(72) Inventor: Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 251 days.

(21) Appl. No.: 15/354,563

(22) Filed: Nov. 17, 2016

(65) Prior Publication Data

US 2017/0150965 A1    Jun. 1, 2017

Related U.S. Application Data

(60) Provisional application No. 62/261,469, filed on Dec. 1, 2015.

(51) Int. Cl.
*A61B 17/068* (2006.01)
*A61B 17/115* (2006.01)
(Continued)

(52) U.S. Cl.
CPC .......... *A61B 17/068* (2013.01); *A61B 17/115* (2013.01); *A61B 17/1155* (2013.01);
(Continued)

(58) Field of Classification Search
CPC ........ F16H 25/14; F16H 25/08; F16H 37/124; F16H 37/126; F16H 25/02; F16H 25/12; F16H 25/20; F16H 2025/209; F16H 2025/2062; F16H 2025/2075; F16H 2025/2081; F16H 2025/2078; F16H 25/2056; A61B 17/068; A61B 17/115; A61B 17/1155; A61B 2017/0046; A61B 2017/00464; A61B 2017/00473; A61B 2017/00477; A61B 2017/00486;
(Continued)

(56) References Cited

U.S. PATENT DOCUMENTS 2,224,905 A * 12/1940 Franz ............... F16H 25/14
                                                           242/482.8
2,586,870 A *  2/1952 Shapiro ............ H01F 21/065
                                                            74/10.85
(Continued)

FOREIGN PATENT DOCUMENTS

CA    2451558 A1    1/2003
CN    1547454 A    11/2004
(Continued)

OTHER PUBLICATIONS

European Search Report dated Mar. 30, 2017, issued in EP Application No. 16201370.
(Continued)

*Primary Examiner* — Jake Cook
*Assistant Examiner* — T. Scott Fix
(74) *Attorney, Agent, or Firm* — Carter, DeLuca & Farrell LLP

(57) ABSTRACT

An adapter assembly for connecting an end effector to a surgical instrument includes first, second, and third drive assemblies configured for converting rotational motion into linear motion. Each of the second and third drive assemblies includes a cam assembly for longitudinally advancing and retracting respective second and third drive members.

21 Claims, 10 Drawing Sheets

(51) Int. Cl.
*F16H 1/16* (2006.01)
*F16H 25/14* (2006.01)
*F16H 25/20* (2006.01)
*F16H 37/12* (2006.01)
*A61B 17/00* (2006.01)

(52) U.S. Cl.
CPC .............. *F16H 1/16* (2013.01); *F16H 25/14* (2013.01); *F16H 25/20* (2013.01); *F16H 37/124* (2013.01); *A61B 2017/0046* (2013.01); *A61B 2017/00464* (2013.01); *A61B 2017/00473* (2013.01); *A61B 2017/00477* (2013.01); *A61B 2017/00486* (2013.01)

(58) Field of Classification Search
CPC ........... A61B 2017/00353; A61B 2017/00367; A61B 2017/00371; A61M 2205/10; A61M 2205/103; A61M 2205/106; B05C 17/01; B05C 17/0103; B05C 17/0116; B05C 17/0133
USPC .......................................... 74/424.71, 424.7
See application file for complete search history.

(56) References Cited

U.S. PATENT DOCUMENTS

| | | | |
|---|---|---|---|
| 2,777,340 A | | 1/1957 | Hettwer et al. |
| 2,957,353 A | | 10/1960 | Babacz |
| 3,070,695 A | * | 12/1962 | Lemmermann ......... G01T 1/166 250/363.01 |
| 3,111,328 A | | 11/1963 | Di Rito et al. |
| 3,242,996 A | * | 3/1966 | Wright .................. B25B 23/145 173/178 |
| 3,688,612 A | * | 9/1972 | Hiroshi .................. B23Q 5/341 82/11.3 |
| 3,695,058 A | | 10/1972 | Keith, Jr. |
| 3,734,515 A | | 5/1973 | Dudek |
| 3,759,336 A | | 9/1973 | Marcovitz et al. |
| 3,798,983 A | * | 3/1974 | Smith ....................... F16H 1/16 74/89.35 |
| 3,816,218 A | * | 6/1974 | Felten ................... B29D 30/32 156/398 |
| 3,996,697 A | * | 12/1976 | Bailey .................... E05F 15/41 49/28 |
| 4,080,844 A | * | 3/1978 | Killian ................. F16H 25/2025 74/89.38 |
| 4,162,399 A | | 7/1979 | Hudson |
| 4,189,950 A | * | 2/1980 | Killian ................. F16H 25/2025 74/89.38 |
| 4,306,671 A | * | 12/1981 | Fisher ................. B05C 17/0103 222/326 |
| 4,606,343 A | | 8/1986 | Conta et al. |
| 4,705,038 A | | 11/1987 | Sjostrom et al. |
| 4,722,685 A | | 2/1988 | de Estrada et al. |
| 4,823,807 A | | 4/1989 | Russell et al. |
| 4,874,181 A | | 10/1989 | Hsu |
| 4,876,794 A | * | 10/1989 | Myers ..................... B25B 7/12 30/252 |
| 5,054,393 A | * | 10/1991 | MacPhee ................ B41F 31/15 101/348 |
| 5,054,836 A | * | 10/1991 | Schulz ................ B25J 15/0206 294/116 |
| 5,104,005 A | * | 4/1992 | Schneider, Jr. ... B05C 17/00553 222/137 |
| 5,129,118 A | | 7/1992 | Walmesley |
| 5,129,570 A | | 7/1992 | Schulze et al. |
| 5,152,744 A | | 10/1992 | Krause et al. |
| 5,281,220 A | * | 1/1994 | Blake, III .............. A61B 17/29 606/113 |
| 5,301,061 A | | 4/1994 | Nakada et al. |
| 5,312,023 A | | 5/1994 | Green et al. |
| 5,326,013 A | | 7/1994 | Green et al. |
| 5,350,355 A | | 9/1994 | Sklar |
| 5,383,874 A | | 1/1995 | Jackson et al. |
| 5,383,880 A | | 1/1995 | Hooven |
| 5,389,098 A | | 2/1995 | Tsuruta et al. |
| 5,395,033 A | | 3/1995 | Byrne et al. |
| 5,400,267 A | | 3/1995 | Denen et al. |
| 5,411,508 A | | 5/1995 | Bessler et al. |
| 5,413,267 A | | 5/1995 | Solyntjes et al. |
| 5,427,087 A | | 6/1995 | Ito et al. |
| 5,433,721 A | | 7/1995 | Hooven et al. |
| 5,467,911 A | | 11/1995 | Tsuruta et al. |
| 5,476,379 A | | 12/1995 | Disel |
| 5,487,499 A | | 1/1996 | Sorrentino et al. |
| 5,518,163 A | | 5/1996 | Hooven |
| 5,518,164 A | | 5/1996 | Hooven |
| 5,526,822 A | | 6/1996 | Burbank et al. |
| 5,529,235 A | | 6/1996 | Boiarski et al. |
| 5,535,934 A | | 7/1996 | Boiarski et al. |
| 5,535,937 A | | 7/1996 | Boiarski et al. |
| 5,540,375 A | | 7/1996 | Bolanos et al. |
| 5,540,706 A | | 7/1996 | Aust et al. |
| 5,542,594 A | | 8/1996 | McKean et al. |
| 5,549,637 A | | 8/1996 | Crainich |
| 5,553,675 A | | 9/1996 | Pitzen et al. |
| 5,562,239 A | | 10/1996 | Boiarski et al. |
| 5,564,615 A | | 10/1996 | Bishop et al. |
| 5,609,560 A | | 3/1997 | Ichikawa et al. |
| 5,626,587 A | | 5/1997 | Bishop et al. |
| 5,632,432 A | | 5/1997 | Schulze et al. |
| 5,645,209 A | | 7/1997 | Green et al. |
| 5,647,526 A | | 7/1997 | Green et al. |
| 5,653,374 A | | 8/1997 | Young et al. |
| 5,658,300 A | | 8/1997 | Bito et al. |
| 5,662,662 A | | 9/1997 | Bishop et al. |
| 5,667,517 A | | 9/1997 | Hooven |
| 5,693,042 A | | 12/1997 | Boiarski et al. |
| 5,704,534 A | | 1/1998 | Huitema et al. |
| 5,713,505 A | | 2/1998 | Huitema |
| 5,762,603 A | | 6/1998 | Thompson |
| 5,779,130 A | | 7/1998 | Alesi et al. |
| 5,782,396 A | | 7/1998 | Mastri et al. |
| 5,782,397 A | | 7/1998 | Koukline |
| 5,792,573 A | | 8/1998 | Pitzen et al. |
| 5,797,536 A | | 8/1998 | Smith et al. |
| 5,820,009 A | | 10/1998 | Melling et al. |
| 5,863,159 A | | 1/1999 | Lasko |
| 5,908,427 A | | 6/1999 | McKean et al. |
| 5,954,259 A | | 9/1999 | Viola et al. |
| 5,964,774 A | | 10/1999 | McKean et al. |
| 5,993,454 A | | 11/1999 | Longo |
| 6,009,773 A | * | 1/2000 | Kato ....................... F16H 25/14 74/569 |
| 6,010,054 A | | 1/2000 | Johnson et al. |
| 6,017,354 A | | 1/2000 | Culp et al. |
| 6,032,849 A | | 3/2000 | Mastri et al. |
| 6,045,560 A | | 4/2000 | McKean et al. |
| 6,090,123 A | | 7/2000 | Culp et al. |
| 6,126,651 A | | 10/2000 | Mayer |
| 6,129,547 A | | 10/2000 | Cise et al. |
| 6,165,169 A | | 12/2000 | Panescu et al. |
| 6,239,732 B1 | | 5/2001 | Cusey |
| 6,241,139 B1 | | 6/2001 | Milliman et al. |
| 6,264,086 B1 | | 7/2001 | McGuckin, Jr. |
| 6,264,087 B1 | | 7/2001 | Whitman |
| 6,302,311 B1 | | 10/2001 | Adams et al. |
| 6,315,184 B1 | | 11/2001 | Whitman |
| 6,321,855 B1 | | 11/2001 | Barnes |
| 6,329,778 B1 | | 12/2001 | Culp et al. |
| 6,343,731 B1 | | 2/2002 | Adams et al. |
| 6,348,061 B1 | | 2/2002 | Whitman |
| 6,368,324 B1 | | 4/2002 | Dinger et al. |
| 6,371,909 B1 | | 4/2002 | Hoeg et al. |
| 6,434,507 B1 | | 8/2002 | Clayton et al. |
| 6,443,973 B1 | | 9/2002 | Whitman |
| 6,461,372 B1 | | 10/2002 | Jensen et al. |
| 6,488,180 B1 | * | 12/2002 | Bayat ................ B05C 17/00553 222/137 |
| 6,488,197 B1 | | 12/2002 | Whitman |
| 6,491,201 B1 | | 12/2002 | Whitman |
| 6,533,157 B1 | | 3/2003 | Whitman |

(56) References Cited

U.S. PATENT DOCUMENTS

| | | |
|---|---|---|
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,673,087 B1 * | 1/2004 | Chang ............ A61B 17/320016 606/170 |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |

(56) References Cited

U.S. PATENT DOCUMENTS

| | | | |
|---|---|---|---|
| 8,652,121 B2 | 2/2014 | Quick et al. | |
| 8,657,174 B2 | 2/2014 | Yates et al. | |
| 8,657,177 B2 | 2/2014 | Scirica et al. | |
| 8,672,206 B2 | 3/2014 | Aranyi et al. | |
| 8,696,552 B2 | 4/2014 | Whitman | |
| 8,708,213 B2 | 4/2014 | Shelton, IV et al. | |
| 8,715,306 B2 | 5/2014 | Faller et al. | |
| 8,758,391 B2 | 6/2014 | Swayze et al. | |
| 8,806,973 B2 | 8/2014 | Ross et al. | |
| 8,808,311 B2 | 8/2014 | Heinrich et al. | |
| 8,820,605 B2 | 9/2014 | Shelton, IV | |
| 8,851,355 B2 | 10/2014 | Aranyi et al. | |
| 8,858,571 B2 | 10/2014 | Shelton, IV et al. | |
| 8,875,972 B2 | 11/2014 | Weisenburgh, II et al. | |
| 8,888,762 B2 | 11/2014 | Whitman | |
| 8,893,946 B2 | 11/2014 | Boudreaux et al. | |
| 8,899,462 B2 | 12/2014 | Kostrzewski et al. | |
| 8,905,289 B2 | 12/2014 | Patel et al. | |
| 8,910,846 B2 * | 12/2014 | Viola | A61B 17/07207 227/175.1 |
| 8,919,630 B2 | 12/2014 | Milliman | |
| 8,931,680 B2 | 1/2015 | Milliman | |
| 8,939,344 B2 | 1/2015 | Olson et al. | |
| 8,950,646 B2 | 2/2015 | Viola | |
| 8,960,519 B2 | 2/2015 | Whitman et al. | |
| 8,961,396 B2 | 2/2015 | Azarbarzin et al. | |
| 8,967,443 B2 | 3/2015 | McCuen | |
| 8,968,276 B2 | 3/2015 | Zemlok et al. | |
| 8,968,337 B2 | 3/2015 | Whitfield et al. | |
| 8,992,422 B2 | 3/2015 | Spivey et al. | |
| 9,016,545 B2 | 4/2015 | Aranyi et al. | |
| 9,023,014 B2 | 5/2015 | Chowaniec et al. | |
| 9,027,423 B1 * | 5/2015 | Cui | F16H 25/20 74/53 |
| 9,033,868 B2 | 5/2015 | Whitman et al. | |
| 9,055,943 B2 | 6/2015 | Zemlok et al. | |
| 9,064,653 B2 | 6/2015 | Prest et al. | |
| 9,072,515 B2 | 7/2015 | Hall et al. | |
| 9,113,847 B2 | 8/2015 | Whitman et al. | |
| 9,113,875 B2 | 8/2015 | Viola et al. | |
| 9,113,876 B2 | 8/2015 | Zemlok et al. | |
| 9,113,899 B2 | 8/2015 | Garrison et al. | |
| 9,216,013 B2 | 12/2015 | Scirica et al. | |
| 9,241,712 B2 | 1/2016 | Zemlok et al. | |
| 9,282,961 B2 | 3/2016 | Whitman et al. | |
| 9,282,963 B2 | 3/2016 | Bryant | |
| 9,295,522 B2 | 3/2016 | Kostrzewski | |
| 9,307,986 B2 | 4/2016 | Hall et al. | |
| 2001/0027321 A1 * | 10/2001 | Gellman | A61B 17/0401 606/104 |
| 2001/0031975 A1 | 10/2001 | Whitman et al. | |
| 2002/0049454 A1 | 4/2002 | Whitman et al. | |
| 2002/0165541 A1 | 11/2002 | Whitman | |
| 2003/0038938 A1 | 2/2003 | Jung et al. | |
| 2003/0165794 A1 | 9/2003 | Matoba | |
| 2004/0034369 A1 | 2/2004 | Sauer et al. | |
| 2004/0111012 A1 | 6/2004 | Whitman | |
| 2004/0133189 A1 | 7/2004 | Sakurai | |
| 2004/0153124 A1 | 8/2004 | Whitman | |
| 2004/0176751 A1 | 9/2004 | Weitzner et al. | |
| 2004/0193146 A1 | 9/2004 | Lee et al. | |
| 2005/0125027 A1 | 6/2005 | Knodel et al. | |
| 2005/0131442 A1 | 6/2005 | Yachia et al. | |
| 2005/0155443 A1 * | 7/2005 | Krozek | F16H 25/125 74/55 |
| 2005/0235764 A1 * | 10/2005 | Johnson | F01B 9/026 74/55 |
| 2006/0142656 A1 | 6/2006 | Malackowski et al. | |
| 2006/0142740 A1 | 6/2006 | Sherman et al. | |
| 2006/0142744 A1 | 6/2006 | Boutoussov | |
| 2006/0151567 A1 * | 7/2006 | Roy | A61B 17/072 227/175.1 |
| 2006/0259073 A1 | 11/2006 | Miyamoto et al. | |
| 2006/0278680 A1 | 12/2006 | Viola et al. | |
| 2006/0284730 A1 | 12/2006 | Schmid et al. | |
| 2007/0023476 A1 | 2/2007 | Whitman et al. | |
| 2007/0023477 A1 | 2/2007 | Whitman et al. | |
| 2007/0027469 A1 | 2/2007 | Smith et al. | |
| 2007/0029363 A1 | 2/2007 | Popov | |
| 2007/0055219 A1 * | 3/2007 | Whitman | A61B 17/00234 606/1 |
| 2007/0084897 A1 | 4/2007 | Shelton et al. | |
| 2007/0102472 A1 | 5/2007 | Shelton | |
| 2007/0152014 A1 | 7/2007 | Gillum et al. | |
| 2007/0175947 A1 | 8/2007 | Ortiz et al. | |
| 2007/0175949 A1 | 8/2007 | Shelton et al. | |
| 2007/0175950 A1 | 8/2007 | Shelton et al. | |
| 2007/0175951 A1 | 8/2007 | Shelton et al. | |
| 2007/0175955 A1 | 8/2007 | Shelton et al. | |
| 2007/0175961 A1 | 8/2007 | Shelton et al. | |
| 2007/0227850 A1 * | 10/2007 | Heravi | B60K 23/08 192/20 |
| 2007/0270784 A1 | 11/2007 | Smith et al. | |
| 2008/0029570 A1 | 2/2008 | Shelton et al. | |
| 2008/0029573 A1 | 2/2008 | Shelton et al. | |
| 2008/0029574 A1 | 2/2008 | Shelton et al. | |
| 2008/0029575 A1 | 2/2008 | Shelton et al. | |
| 2008/0058801 A1 | 3/2008 | Taylor et al. | |
| 2008/0109012 A1 | 5/2008 | Falco et al. | |
| 2008/0110958 A1 | 5/2008 | McKenna et al. | |
| 2008/0147089 A1 | 6/2008 | Loh et al. | |
| 2008/0167736 A1 | 7/2008 | Swayze et al. | |
| 2008/0185419 A1 | 8/2008 | Smith et al. | |
| 2008/0188841 A1 | 8/2008 | Tomasello et al. | |
| 2008/0197167 A1 | 8/2008 | Viola et al. | |
| 2008/0208195 A1 | 8/2008 | Shores et al. | |
| 2008/0237296 A1 | 10/2008 | Boudreaux et al. | |
| 2008/0251561 A1 | 10/2008 | Eades et al. | |
| 2008/0255413 A1 | 10/2008 | Zemlok et al. | |
| 2008/0255607 A1 | 10/2008 | Zemlok | |
| 2008/0262654 A1 | 10/2008 | Omori et al. | |
| 2008/0308603 A1 | 12/2008 | Shelton et al. | |
| 2009/0012533 A1 | 1/2009 | Barbagli et al. | |
| 2009/0090763 A1 | 4/2009 | Zemlok et al. | |
| 2009/0099876 A1 | 4/2009 | Whitman | |
| 2009/0138006 A1 | 5/2009 | Bales et al. | |
| 2009/0171147 A1 | 7/2009 | Lee et al. | |
| 2009/0182193 A1 | 7/2009 | Whitman et al. | |
| 2009/0209946 A1 | 8/2009 | Swayze et al. | |
| 2009/0209990 A1 | 8/2009 | Yates et al. | |
| 2009/0254094 A1 | 10/2009 | Knapp et al. | |
| 2009/0299141 A1 | 12/2009 | Downey | |
| 2010/0023022 A1 | 1/2010 | Zeiner et al. | |
| 2010/0069942 A1 | 3/2010 | Shelton, IV | |
| 2010/0160821 A1 * | 6/2010 | Parihar | A61B 10/0275 600/567 |
| 2010/0193568 A1 | 8/2010 | Scheib et al. | |
| 2010/0211053 A1 | 8/2010 | Ross et al. | |
| 2010/0225073 A1 | 9/2010 | Porter et al. | |
| 2010/0320252 A1 * | 12/2010 | Viola | A61B 17/07207 227/176.1 |
| 2011/0071508 A1 | 3/2011 | Duval et al. | |
| 2011/0077673 A1 | 3/2011 | Grubac et al. | |
| 2011/0121049 A1 | 5/2011 | Malinouskas et al. | |
| 2011/0125138 A1 | 5/2011 | Malinouskas et al. | |
| 2011/0139851 A1 | 6/2011 | McCuen | |
| 2011/0155783 A1 | 6/2011 | Rajappa et al. | |
| 2011/0155786 A1 | 6/2011 | Shelton, IV | |
| 2011/0172648 A1 | 7/2011 | Jeong | |
| 2011/0174009 A1 | 7/2011 | Lizuka et al. | |
| 2011/0174099 A1 * | 7/2011 | Ross | A61B 17/072 74/89.32 |
| 2011/0184245 A1 | 7/2011 | Xia et al. | |
| 2011/0204119 A1 | 8/2011 | McCuen | |
| 2011/0218522 A1 | 9/2011 | Whitman | |
| 2011/0247449 A1 * | 10/2011 | Parker | F16H 25/14 74/569 |
| 2011/0276057 A1 | 11/2011 | Conlon et al. | |
| 2011/0290854 A1 | 12/2011 | Timm et al. | |
| 2011/0295242 A1 | 12/2011 | Spivey et al. | |
| 2011/0295269 A1 | 12/2011 | Swensgard et al. | |
| 2012/0000962 A1 | 1/2012 | Racenet et al. | |
| 2012/0074199 A1 | 3/2012 | Olson et al. | |

(56) References Cited

U.S. PATENT DOCUMENTS

| | | |
|---|---|---|
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0215220 A1* | 8/2012 | Manzo ............... A61B 18/1445 606/46 |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0265095 A1* | 10/2012 | Fiebig ............... A61B 10/0275 600/567 |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0260720 A1* | 9/2014 | Hartranft ............... F16H 21/22 74/42 |
| 2014/0276932 A1 | 9/2014 | Williams et al. |
| 2014/0277334 A1 | 9/2014 | Yu et al. |
| 2014/0299647 A1 | 10/2014 | Scirica et al. |
| 2014/0303668 A1* | 10/2014 | Nicholas ............. A61B 17/07207 606/207 |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0035658 A1* | 2/2015 | Provancher ............. G06F 3/016 340/407.1 |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1* | 11/2015 | Kostrzewski ......... A61B 17/0469 606/144 |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | | |
|---|---|---|---|
| CN | 1957854 | A | 5/2007 |
| CN | 101495046 | A | 7/2009 |
| CN | 102247182 | A | 11/2011 |
| CN | 103498904 | A * | 1/2014 |
| CN | 103498905 | A * | 1/2014 |
| DE | 102008053842 | A1 | 5/2010 |
| EP | 0705571 | A1 | 4/1996 |
| EP | 1563793 | A1 | 8/2005 |
| EP | 1769754 | A1 | 4/2007 |
| EP | 2316345 | A1 | 5/2011 |
| EP | 2446834 | A1 | 5/2012 |
| EP | 2668910 | A2 | 12/2013 |
| ES | 2333509 | A1 | 2/2010 |
| JP | 2005-125075 | A | 5/2005 |
| KR | 20120022521 | A | 3/2012 |
| WO | 2011/108840 | A2 | 9/2011 |
| WO | 2012/040984 | A1 | 4/2012 |

OTHER PUBLICATIONS

Extended European Search Report corresponding to counterpart International Application No. EP 14 18 4882.0 dated May 12, 2015.
Canadian Office Action corresponding to counterpart International Application No. CA 2640399 dated May 7, 2015.
Japanese Office Action corresponding to counterpart International Application No. JP 2011-197365 dated Mar. 23, 2015.
Japanese Office Action corresponding to counterpart International Application No. JP 2011-084092 dated May 20, 2015.
Japanese Office Action corresponding to counterpart International Application No. JP 2014-148482 dated Jun. 2, 2015.
Extended European Search Report corresponding to counterpart International Application No. EP 14 18 9358.6 dated Jul. 8, 2015.
Extended European Search Report corresponding to counterpart International Application No. EP 14 19 6148.2 dated Apr. 23, 2015.
Partial European Search Report corresponding to counterpart International Application No. EP 14 19 6704.2 dated May 11, 2015.
Australian Office Action corresponding to counterpart International Application No. AU 2010241367 dated Aug. 20, 2015.
Partial European Search Report corresponding to counterpart International Application No. EP 14 19 9783.3 dated Sep. 3, 2015.
Extended European Search Report corresponding to counterpart International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.

(56) References Cited

OTHER PUBLICATIONS

European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 38071 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
Australian Examination Report No. 1 corresponding to International Application No. AU 2013205872 dated Oct. 19, 2016.
Australian Examination Report from Appl. No. AU 2013205840 dated Nov. 3, 2016.
European Search Report corresponding to EP 15 184 915.5-1654 dated Sep. 16, 2016.
European Office Action dated May 10, 2019, issued in EP Appln. No. 16201370.

* cited by examiner

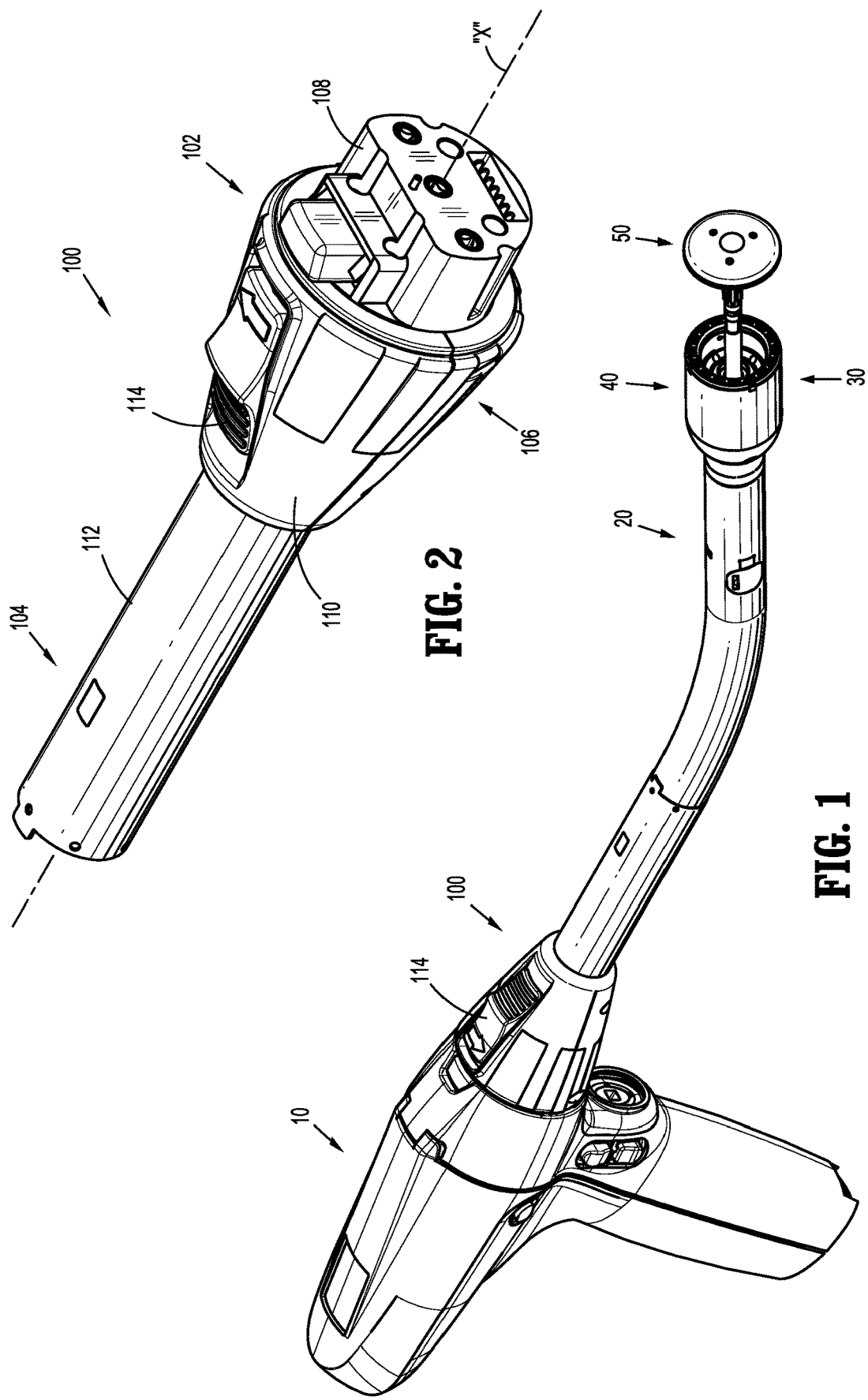

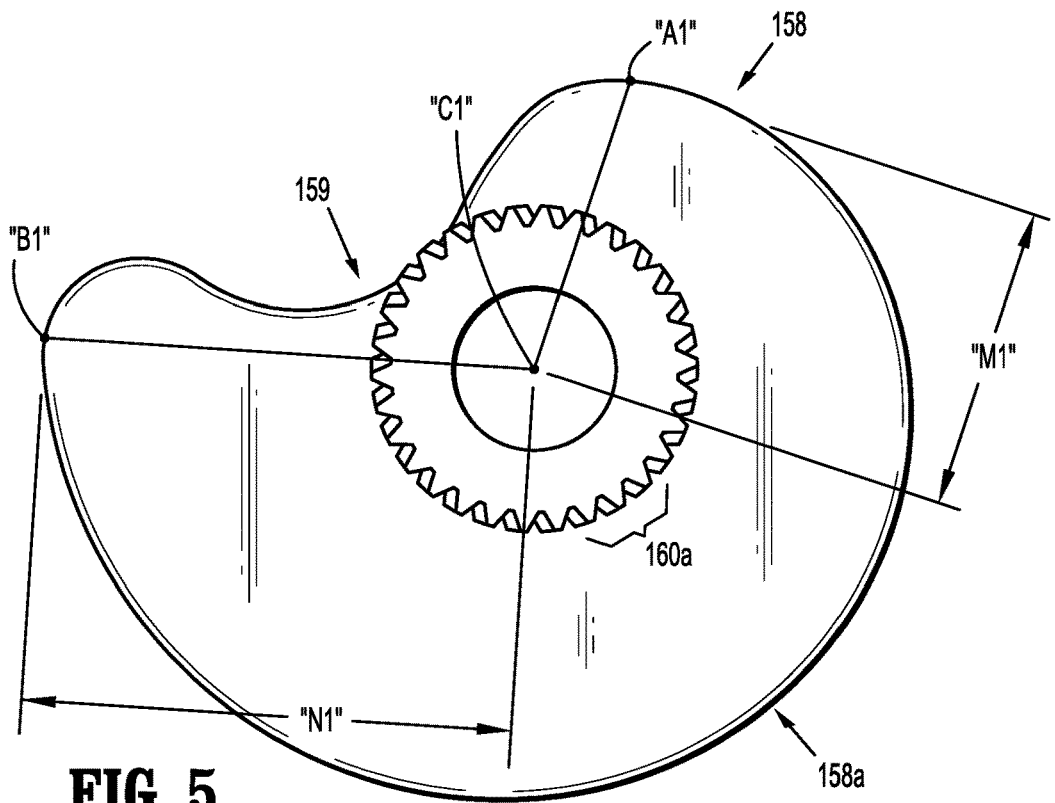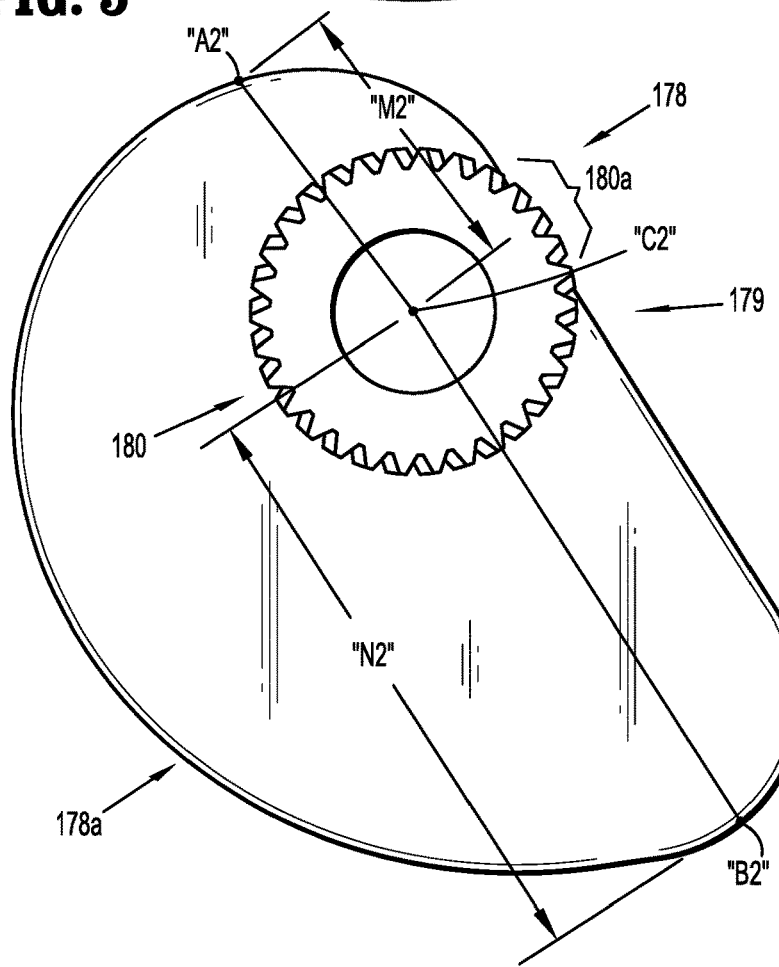

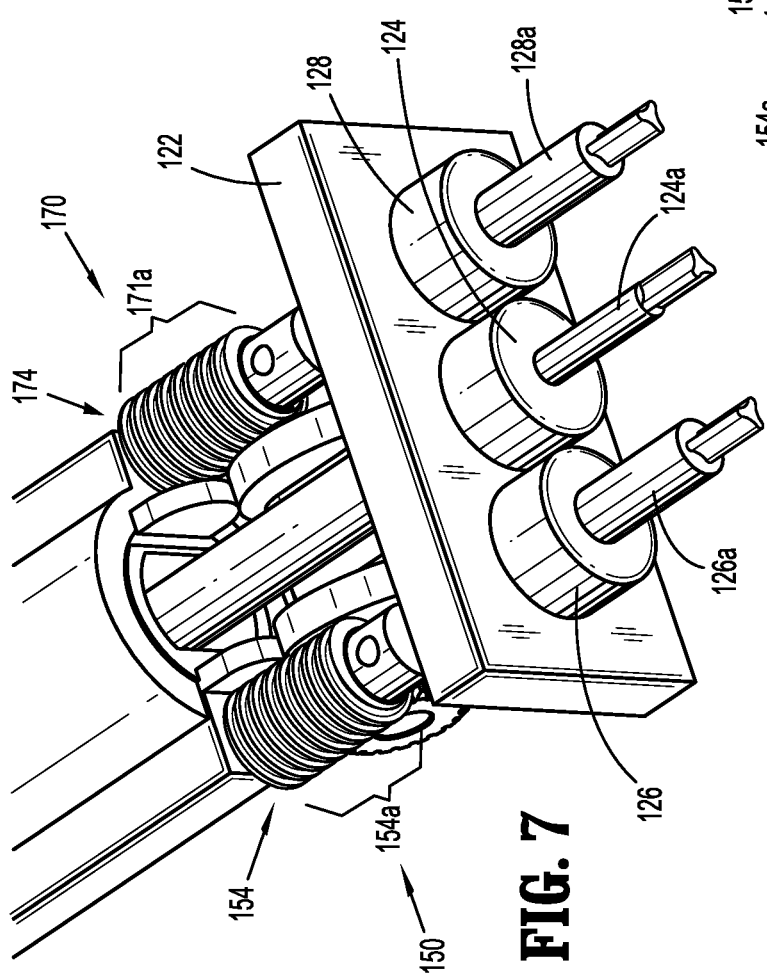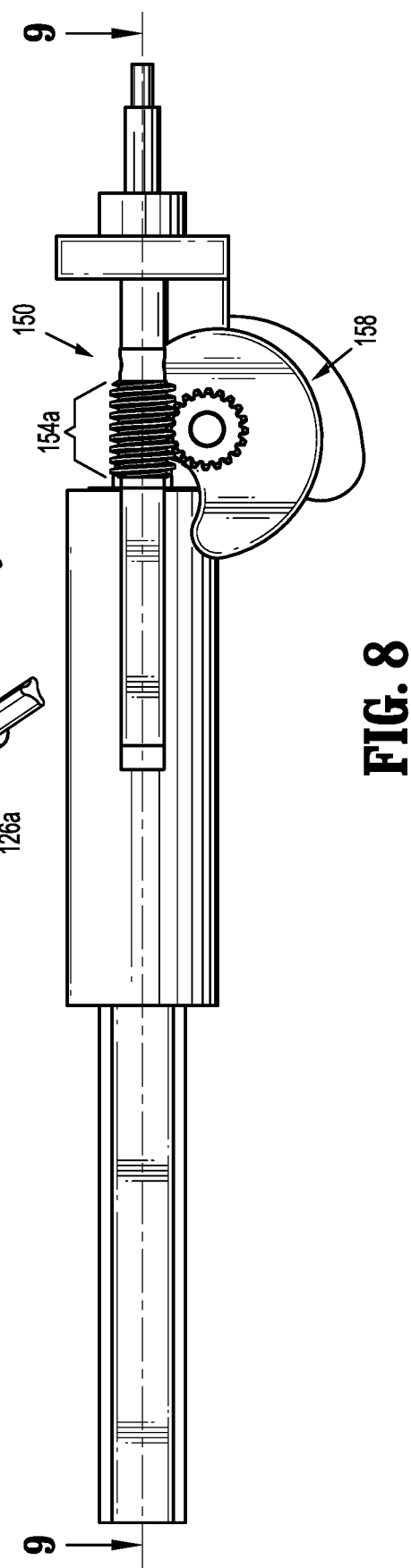

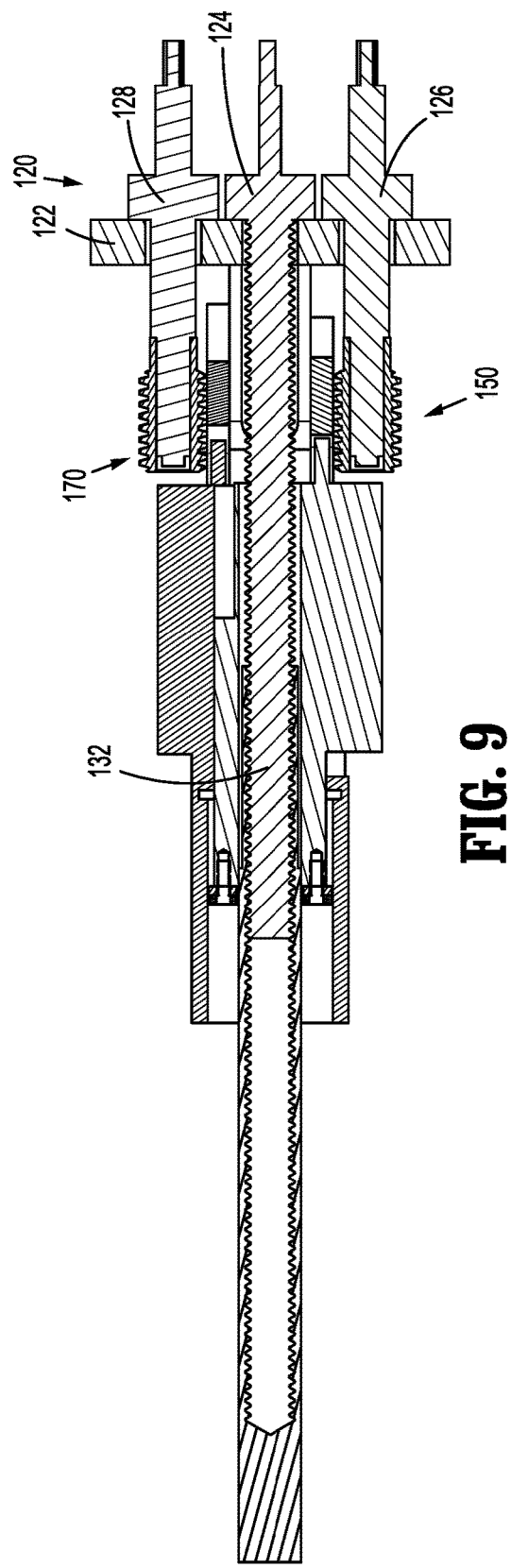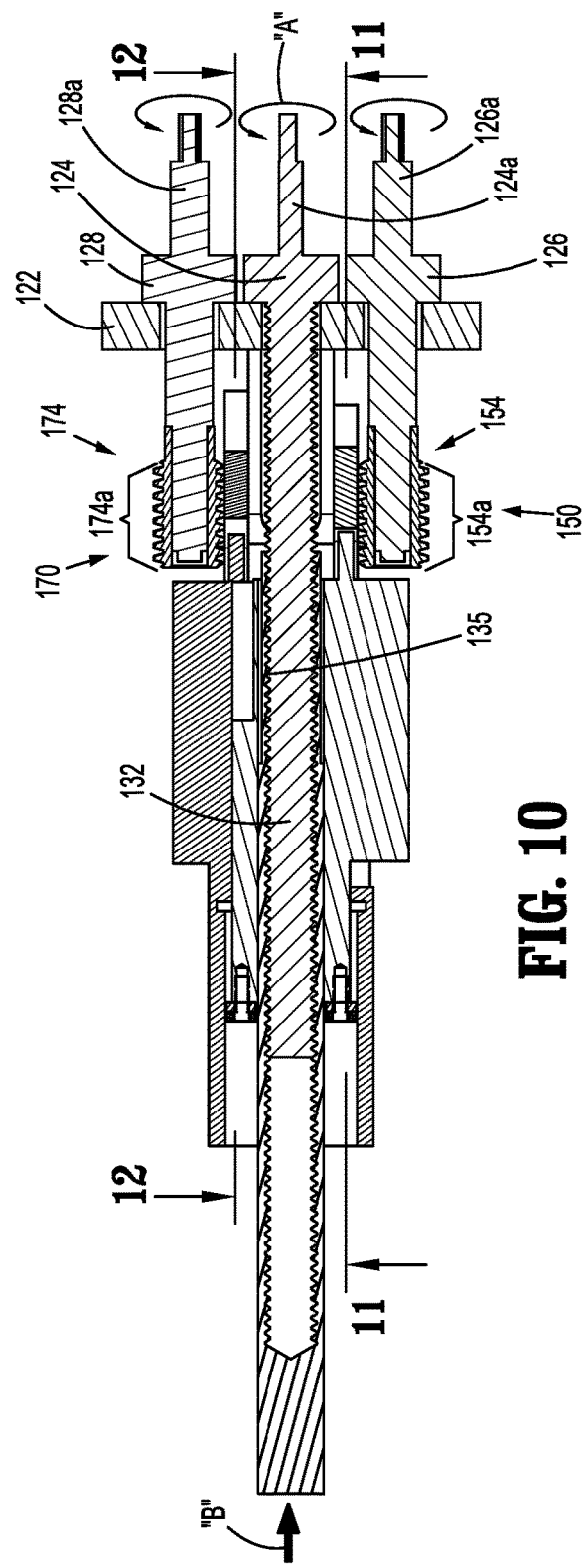
FIG. 9
FIG. 10

ADAPTER ASSEMBLY FOR SURGICAL DEVICE

CROSS-REFERENCE TO RELATED APPLICATIONS

This application claims the benefit of and priority to U.S. Provisional Patent Application No. 62/261,469, filed Dec. 1, 2015, the entire disclosure of which is incorporated by reference herein.

BACKGROUND

1. Technical Field

The present disclosure relates generally to powered surgical devices. More specifically, the present disclosure relates to adapter assemblies for selectively connecting end effectors to actuation units of powered surgical devices.

2. Background of Related Art

Powered devices for use in surgical procedures typically convert rotational motion from a handle assembly to linear motion for effectuating one or more functions, e.g., clamping, stapling, cutting. To permit reuse of the handle assemblies of these powered surgical devices and so that the handle assembly may be used with a variety of end effectors, adapter assemblies have been developed for selective attachment to the handle assemblies and to a variety of end effectors. Following use, the adapter assembly may be disposed of along with the end effector. In some instances, the adapter assembly may be sterilized for reuse.

SUMMARY

An adapter assembly for operably connecting an end effector to a powered surgical instrument is provided. The adapter assembly includes a drive coupling assembly, a first drive assembly operably connected to the drive coupling assembly, a second drive assembly operably connected to the drive coupling assembly, and a third drive assembly operably connected to the drive coupling assembly. The first drive assembly includes a drive screw, the second drive assembly includes a first cam assembly, and, the third drive assembly includes a second cam assembly.

In embodiments, the second drive assembly may include a second drive member operably connected to the first cam assembly. The first cam assembly may be rotatable from a first orientation to a second to move the second drive member from a proximal position to a distal orientation. The third drive assembly may include a third drive member operably connected to the second cam assembly. The second cam assembly may be movable from a first orientation to a second orientation to move the third drive member from a proximal position to a distal position.

Each of the second and third drive members may include a tubular portion. The tubular portion of the third drive member may be slidably disposed within the tubular portion of the second drive member. Each of the second and third drive assemblies may include a guide member. Each of the second and third drive members may include a guide portion slidably disposed within the respective guide members. The first drive member may be slidably disposed within the tubular portion of the second drive member.

In embodiments, the drive coupling assembly may include a thruster plate and first, second, and third connector members. The first connector member may be operably connected to the drive screw. The second connector member may be operably connected to the first cam assembly. The third connector member may be operably connected to the second cam assembly.

The first cam assembly may include a drive shaft, a worm drive operably disposed on the drive shaft, a cam member, and a worm gear operably disposed on the cam member. The first cam assembly may include a cam member having an eccentric outer surface. The second drive member may include an engagement portion for engaging the eccentric outer surface. The eccentric outer surface of the cam member may include a first point a first distance from a central axis of the cam member and a second point a second distance from the central axis. The second distance may be greater than the first distance. A difference between the second distance and the first distance may be a distance of travel of the second drive member. Movement of the first drive member may perform a first function, movement of the second drive member may perform a second function, and movement of the third member may perform a third function.

In one embodiment, the adapter assembly includes a rotation assembly having a base and a rotation handle rotatably secured to the base. The adapter assembly may also include a sleeve fixedly secured to the rotation handle. The first, second, and third drive assemblies of the adapter assembly may be secured within the base.

BRIEF DESCRIPTION OF THE DRAWINGS

Embodiments of the present disclosure are described herein with reference to the accompanying drawings, wherein:

FIG. 1 is a perspective view of an adapter assembly, in accordance with an embodiment of the present disclosure, an exemplary electromechanical handle assembly, an exemplary extension assembly, and an exemplary end effector;

FIG. 2 is a perspective view of the adapter assembly of FIG. 1;

FIG. 5 is a perspective side view of a first cam member of a second drive assembly of the drive mechanism of FIG. 3;

FIG. 6 is a perspective, side view of a second cam member of a third drive assembly of the drive mechanism of FIG. 3;

FIG. 7 is a perspective top view of a proximal end of the drive mechanism of FIG. 3, with each of the first, second, and third drive assemblies in their respective first positions;

FIG. 8 is side view of the drive mechanism of FIG. 3, with each of the first, second, and third drive assemblies in their first positions;

FIG. 9 is a cross-sectional top view of the drive assembly of FIG. 3 taken along section line 9-9 of FIG. 8 with each of the first, second, and third drive assemblies in their first positions;

FIG. 10 is a cross-sectional top view of the drive assembly of FIG. 3 taken along section line 9-9 of FIG. 8 with the first drive assembly in a second position, and each of the second and third drive assemblies in their first positions;

DETAILED DESCRIPTION OF EMBODIMENTS

Figure 3:
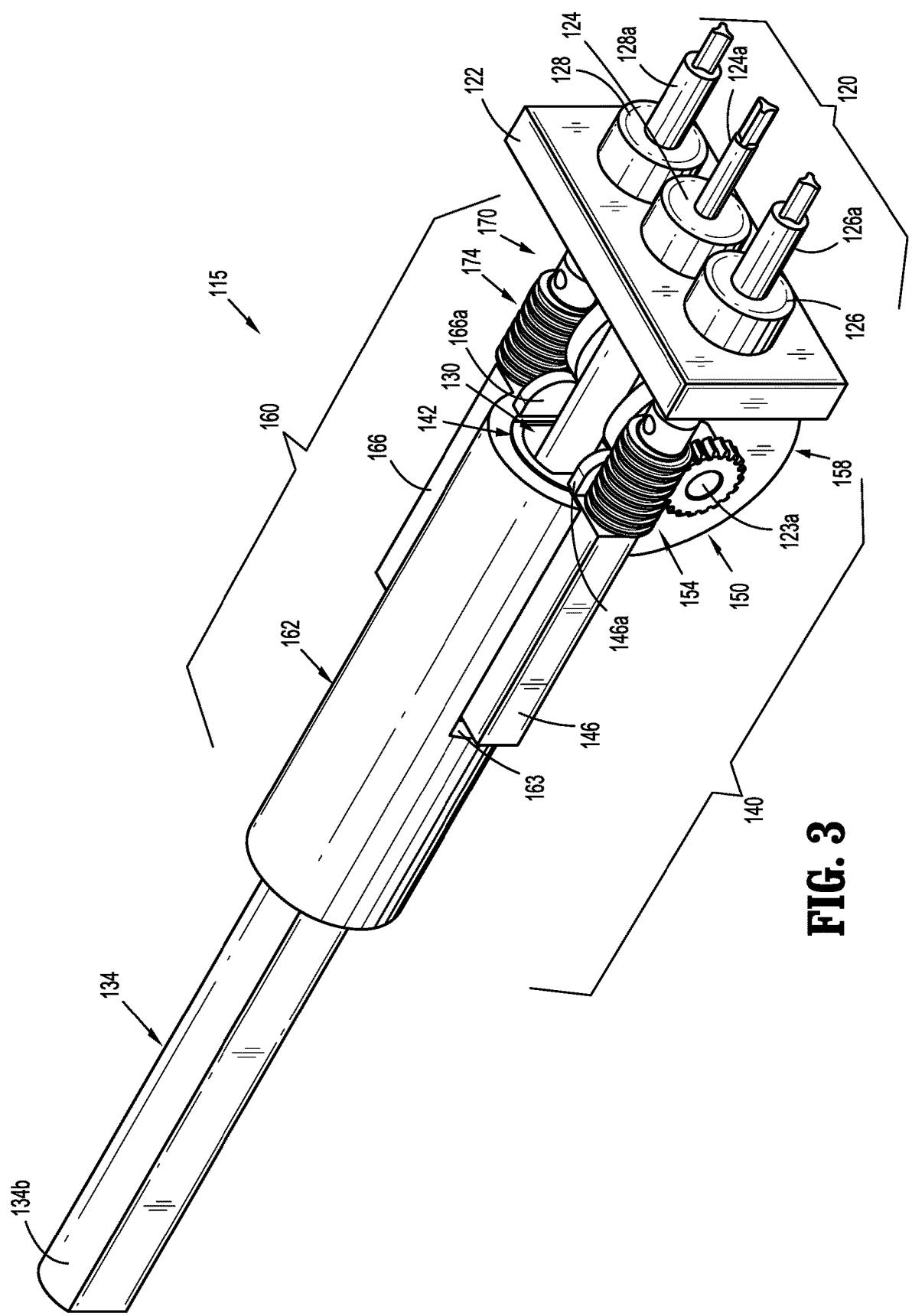
FIG. 3 is a perspective view of a drive mechanism of the adapter assembly of FIG. 1.

Embodiments of the presently disclosed adapter assembly for surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

With reference to FIGS. 1 and 2, an adapter assembly in accordance with an embodiment of the present disclosure, shown generally as adapter assembly 100, is configured for selective connection to a powered handheld electromechanical instrument shown, generally as surgical device 10. As illustrated in FIG. 1, the surgical device 10 is configured for selective connection with the adapter assembly 100, and, in turn, the adapter assembly 100 is configured for selective connection with an extension assembly 20. The extension assembly 20 is configured for selective connection with a tool assembly or end effector, e.g. tool assembly 30, which may, in exemplary embodiments, include a loading unit 40 and an anvil assembly 50, for applying a circular array of staples (not shown) to tissue (not shown).

For a detailed description of the structure and function of an exemplary electromechanical instrument, please refer to commonly owned U.S. Pat. Appl. Publ. No. 2012/0253329, the content of which is incorporated by reference herein in its entirety.

With continued reference to FIG. 2, the adapter assembly 100 includes a proximal portion 102 and a distal portion 104. The proximal portion 102 includes a rotation assembly 106 having a base 108, and a rotation handle 110 rotatable relative to the base 108 about a longitudinal axis "x" of the adapter assembly 100. The distal portion 104 includes a sleeve 112 fixedly secured to the rotation handle 110. Rotation of the rotation handle 110 causes rotation of the sleeve 112. In this manner, an end effector, e.g. tool assembly 30 (FIG. 1), secured to the distal portion 104 of the adapter assembly 100, or an end effector secured to an extension assembly, e.g., extension assembly 20 (FIG. 1), which is secured to the distal portion 104 of the adapter assembly 100 is rotatable about the longitudinal axis "x" independent of movement of the surgical device 10 (FIG. 1) to which adapter assembly 100 is attached.

Still referring to FIG. 2, a latch 114 is mounted to the rotation handle 110 and selectively secures the rotation handle 110 in a fixed orientation about the longitudinal axis "x". The latch 114 is configured to lock the rotation handle 110 relative to the base 108. Proximal movement of the latch 114 disengages the latch 114 from the base 108 to permit rotation of the rotation handle 110 relative to the base 108. For a detailed description of an exemplary rotation assembly and latch mechanism, please refer to commonly owned U.S. Provisional Patent Application Ser. No. 62/066,518, filed Oct. 21, 2014, the content of which is incorporated by reference herein in its entirety.

With additional reference to FIG. 3, the adapter assembly 100 includes a drive mechanism 115 (FIG. 3) for effecting actuation of an end effector, e.g., tool assembly 30 (FIG. 1), secured to the distal portion 104 of the adapter assembly 100 and/or an end effector, e.g., tool assembly 30, secured to an extension assembly, e.g., the extension assembly 20 (FIG. 1), which is secured to the distal portion 104 of the adapter assembly 100. The drive mechanism 115 is configured to transfer rotational motion from the surgical device 10 (FIG. 1) to linear motion to effect actuation of an end effector. More specifically, the drive mechanism 115 includes a drive coupling assembly 120 (FIG. 3), and first, second, and third drive assemblies 130, 140, 160 operably connected to the drive coupling assembly 120 for transferring rotation movement of respective first, second, and third drive shafts (not shown) of the surgical device 10 (FIG. 1) to respective first, second, and third linear movement for effecting first, second, and third actuations of an attached end effector, e.g. tool assembly 30 (FIG. 1), for performing respective first, second, and third operations of the tool assembly 30, e.g., clamping, stapling, and cutting.

Figure 4:
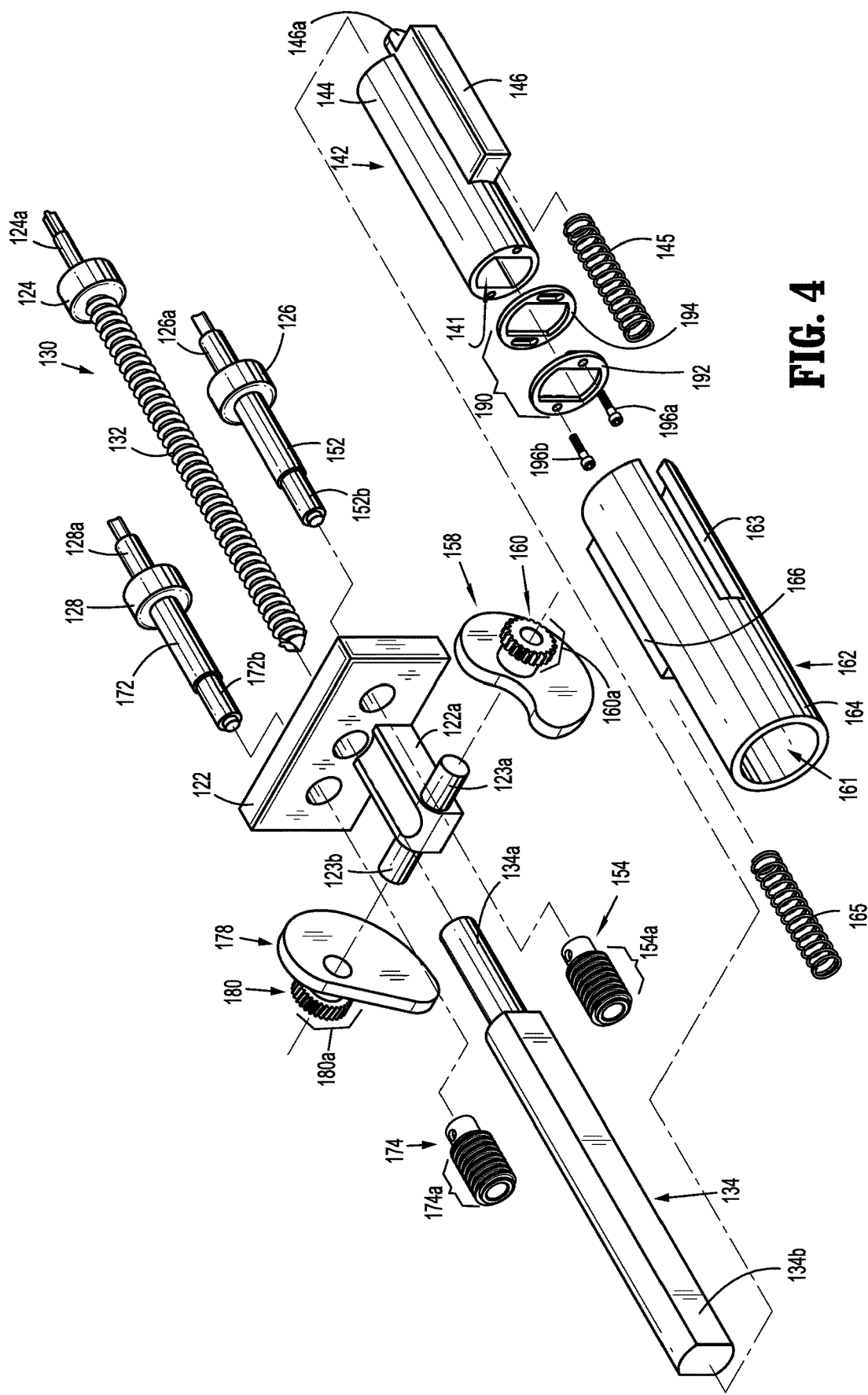
FIG. 4 is a perspective, separated view of the drive mechanism of FIG. 3.

With particular reference to FIGS. 3 and 4, the drive coupling assembly 120 is operably supported within the base 108 (FIG. 2) of the rotation assembly 106 (FIG. 2) and includes a thruster plate 122, and first, second, and third connector members 124, 126, 128 rotatably supported through the thruster plate 122. Proximal ends 124a, 126a, 128a of the respective first, second, and third connector members 124, 126, 128 are configured for operable connection with the respective first, second, and third drive shafts (not shown) of a surgical device, e.g., the surgical device 10 (FIG. 1). A flange 122a (FIG. 4) extends distally from the thruster plate 122 and includes first and second pivot members 123a, 123b (FIG. 4).

The first drive assembly 130 includes a drive screw 132 integrally formed with or fixedly coupled to the first connector member 124 of the drive coupling assembly 120 and extending distally therefrom, and a first drive member 134 longitudinally movable relative to the drive screw 132. Specifically, a proximal end 134a of the first drive member 134 defines a threaded longitudinal opening 135 (FIG. 10) through which the drive screw 132 is received. Rotation of the drive screw 132 in a first direction causes the first drive member 134 to move proximally, i.e., retract, and rotation of the drive screw 132 in a second direction causes the first drive member 134 to move in a distal direction, i.e., advance. As will be described in further detail below, a distal end 134b of the first drive member 134 is operably connectable to a drive member (not shown) of an anvil assembly, e.g., the anvil assembly 50 (FIG. 1), of an end effector, e.g., tool assembly 30 (FIG. 1), to perform a first function, e.g., clamping of tissue.

Still referring to FIGS. 3 and 4, the second drive assembly 140 (FIG. 3) includes a second drive member 142, and a first cam assembly 150 operably disposed between the second connector member 126 of the drive coupling assembly 120 and the second drive member 142. The second drive member 142 includes a tubular portion 144 and a guide portion 146 secured to the tubular portion 144. An engagement portion 146a extends proximally from the guide portion 146 and engages a cam member 158 of a first cam assembly 150. The guide portion 146 of the second drive member 142 may be slidably disposed within a first guide member (not shown), or within a first groove (not shown) of the sleeve 112 (FIG.

2), to maintain the second drive member 142 in axial alignment with the longitudinal axis "x" (FIG. 2) of the adapter assembly 100 (FIG. 2) as operation of the first cam assembly 150 longitudinally translates the second drive member 142 within the sleeve 112. The tubular portion 144 of the second drive member 142 defines a longitudinal opening 141 through which the first drive member 134 of the first drive assembly 130 is received. The second drive member 142 is biased in a proximal direction by a spring 145 (FIG. 4) or other biasing means.

With particular reference to FIG. 4, the first cam assembly 150 includes a drive shaft 152 integrally formed with or fixedly coupled to the second connector member 126 of the drive coupling assembly 120, a worm drive 154 disposed adjacent a distal end 152b of the drive shaft 152, and a cam member 158 rotatably supported relative to the drive shaft 152 on the first pivot member 123a extending from the flange 122a of the thruster plate 122. The cam member 158 includes a worm gear 160 integrally formed with or fixedly coupled thereto. The cam member 158 and the drive shaft 152 are positioned such that teeth 160a of the worm gear 160 operably engage a thread 154a of the worm drive 154. Rotation of the drive shaft 152 in a first direction causes rotation of the cam member 158 in a counter-clockwise direction and rotation of the drive shaft 152 in a second direction causes rotation of the cam member 158 in a clockwise direction.

With particular reference to FIG. 5, the cam member 158 of the first cam assembly 150 (FIG. 3) defines a central axis "C1" and includes an eccentric outer surface 158a. More particularly, a first point "A1" on the eccentric outer surface 158a of the cam member 158 is a first distance "M1" from the central axis "C1" of the cam member 158 and a second point "B1" on the eccentric outer surface 158a of the cam member 158 is a second distance "N1" from the central axis "C1". The second distance "N1" is greater than the first distance "M1". As shown in FIG. 5, when viewed in a clockwise direction, the distance between the eccentric outer surface 158a of the cam member 158 and the central axis "C1" of the cam member 158 gradually increases from the first point "A1" to the second point "B1".

As will become apparent, the difference between the first distance "M1" and the second distance "N1" is the distance in which the second drive member 142 is moved during actuation of the first cam assembly 150. This distance coincides with a distance required to move, for example, a cutting assembly (not shown) of the loading unit 40 (FIG. 1) to cause the cutting of tissue. The eccentric outer surface 158a of the cam member 158 defines a transition zone 159 between the first point "A1" and the second point "B1" in the counter-clockwise direction.

As will be described in further detail below, the second drive member 142 is in a proximal-most position when the engagement portion 146a of the second drive member 142 engages the eccentric outer surface 158a of the cam member 158 within the transition zone 159. As the cam member 158 rotates in a counter-clockwise direction, as indicated by arrow "D" in FIG. 7, the second drive member 142 moves from the proximal-most position (FIG. 7) when in the transition zone 159, to a distal-most position (FIG. 8) to effect a second function, i.e., cutting of tissue.

With continued reference to FIGS. 3 and 4, the third drive assembly 160 includes a third drive member 162, and a second cam assembly 170 operably disposed between the third connector member 128 of the drive coupling assembly 120 and the third drive member 162. The third drive member 162 includes a tubular portion 164 and a guide portion 166 secured to the tubular portion 164. An engagement portion 166a extends proximally from the guide portion 166 and engages a cam member 178 of the second cam assembly 170. The guide portion 166 of the third drive member 162 may be slidably disposed within a second guide member (not shown), or within a second groove (not shown) of the sleeve 112 (FIG. 2), to maintain the third drive member 162 in axial alignment with the longitudinal axis "x" (FIG. 2) of the adapter assembly 100 (FIG. 2) as operation of the second cam assembly 170 longitudinally translates the second drive member 162 within the sleeve 112. The tubular portion 164 of the third drive member 162 defines a longitudinal opening 161 through which the first and second drive members 134, 142 of the respective first and second drive assemblies 130, 140 are received and a longitudinal slot 163 through with the guide portion 146 of the second drive member 142 is received. The third drive member 162 is biased in a proximal direction by a spring 165 or other biasing means.

The second cam assembly 170 includes a drive shaft 172 integrally formed with or fixedly coupled to the third connector member 128 of the drive coupling assembly 120, a worm drive 174 disposed adjacent a distal end 172b of the drive shaft 172, a bearing assembly 176 rotatably supporting the distal end 172b of the drive shaft 172, and a cam member 178 rotatably supported relative to the drive shaft 172 on the second pivot member 123b (FIG. 4) extending from the flange 122a of the thruster plate 122. The cam member 178 includes a worm gear 180 integrally formed with or fixedly coupled thereto. The cam member 178 and the drive shaft 172 are positioned such that teeth 180a (FIG. 6) of the worm gear 180 operably engage a thread 174a of the worm drive 174. Rotation of the drive shaft 172 in a first direction causes rotation of the cam member 178 in a counter-clockwise direction and rotation of the drive shaft 172 in a second direction causes rotation of the cam member 178 in a clockwise direction.

With particular reference to FIG. 6, the cam member 178 of the second cam assembly 170 defines a central axis "C2" and includes an eccentric outer surface 178a. More particularly, a first point "A2" on the eccentric outer surface 178a of the cam member 178 is a first distance "M2" from the central axis "C2" of the cam member 178 and a second point "B2" on the eccentric outer surface 178a is a second distance "N2" from the central axis "C2". The second distance "N2" is greater than the first distance "M2". When viewed in a counter-clockwise direction, the distance between the eccentric outer surface 178a of the cam member 178 and the central axis "C2" of the cam member 178 gradually increases from the first point "A2" to the second point "B2". The difference between the first distance "M2" and the second distance "N2" is the distance required to, for example, move a stapling assembly (not shown) of the loading unit 40 (FIG. 1) to cause the stapling of tissue. The eccentric outer surface 178a of the cam member 178 defines a transition zone 179 between the first point "A2" and the second point "B2" in the counter-clockwise direction.

Although shown as having different configurations, it is envisioned that the first and second cam members 158, 178 of the respective first and second cam assemblies 150, 170 may be the same size and/or configuration. It is further envisioned that each of the first and second cam assemblies 150, 170 may be modified to adjust the rate at which the respective second and third drive members 142, 162 move relative to each other. For example, the thread 154a of the worm drive 154 of the first cam assembly 150 may include a different pitch than the thread 174a of the worm drive 174 of the second cam assembly 170 and/or the number of teeth 160a of the worm gear 160 of the first cam assembly 150 may be different than the number of teeth 180a of the worm gear 180 of the second cam assembly 170 such that the first and second cams 158, 178 rotate at different rates.

With continued reference to FIG. 4, the drive mechanism 115 further includes a seal assembly 190 disposed on a distal end of the second drive member 142 of the second drive assembly 140. The seal assembly 190 includes a seal member 192, and a seal housing 194 for supporting the seal member 192. A pair of fasteners, e.g., screws 196a, 196b, secure the seal assembly 190 to the second drive member 142 of the second drive assembly 140.

The operation of the drive mechanism 115 will now be described with reference to the figures. Referring initially to FIGS. 7-9, the drive mechanism 115 is shown with the first, second, and third drive assemblies 130, 140, 170 in first or initial positions. In the first positions, the first drive member 134 of the first drive assembly 130 is in a distal-most or fully-extended position, and each of the second and third drive members 142, 162 are in a proximal-most or fully-retracted position. When, for example, the anvil assembly 50 (FIG. 1) of the tool assembly 30 (FIG. 1) is operably secured to the first drive member 134, in the first position, the anvil assembly 50 is spaced from the loading unit 40 (FIG. 1), as shown in FIG. 1.

Although shown and described with the first drive member 134 of the first drive assembly 130 in a distal-most position when the first drive assembly 130 is in the first position, it is envisioned that the operation of an end effector (not shown) secured to the adapter assembly 100 (FIG. 1) may require the first drive member 134 of the first drive assembly 130 to be in a proximal-most or fully-retracted position, or at a location somewhere between the distal-most and proximal-most positions, when the first drive assembly 130 is in the first position. Similarly, although shown and described with the second and third drive members 142, 162 of the respective second and third drive assemblies 140, 160 in a proximal-most position when the second and third drive assemblies 140, 160 are in the first position, it is envisioned that the operation of an end effector secured to the adapter assembly 100 (FIG. 1) may require either or both of the second and third drive members 142, 162 of the respective second and third drive assemblies 140, 160 to be in a distal-most position, or at a location somewhere between the proximal-most and distal-most positions, when the second and/or third drive assemblies 140, 160 are in the first position.

Figure 11:
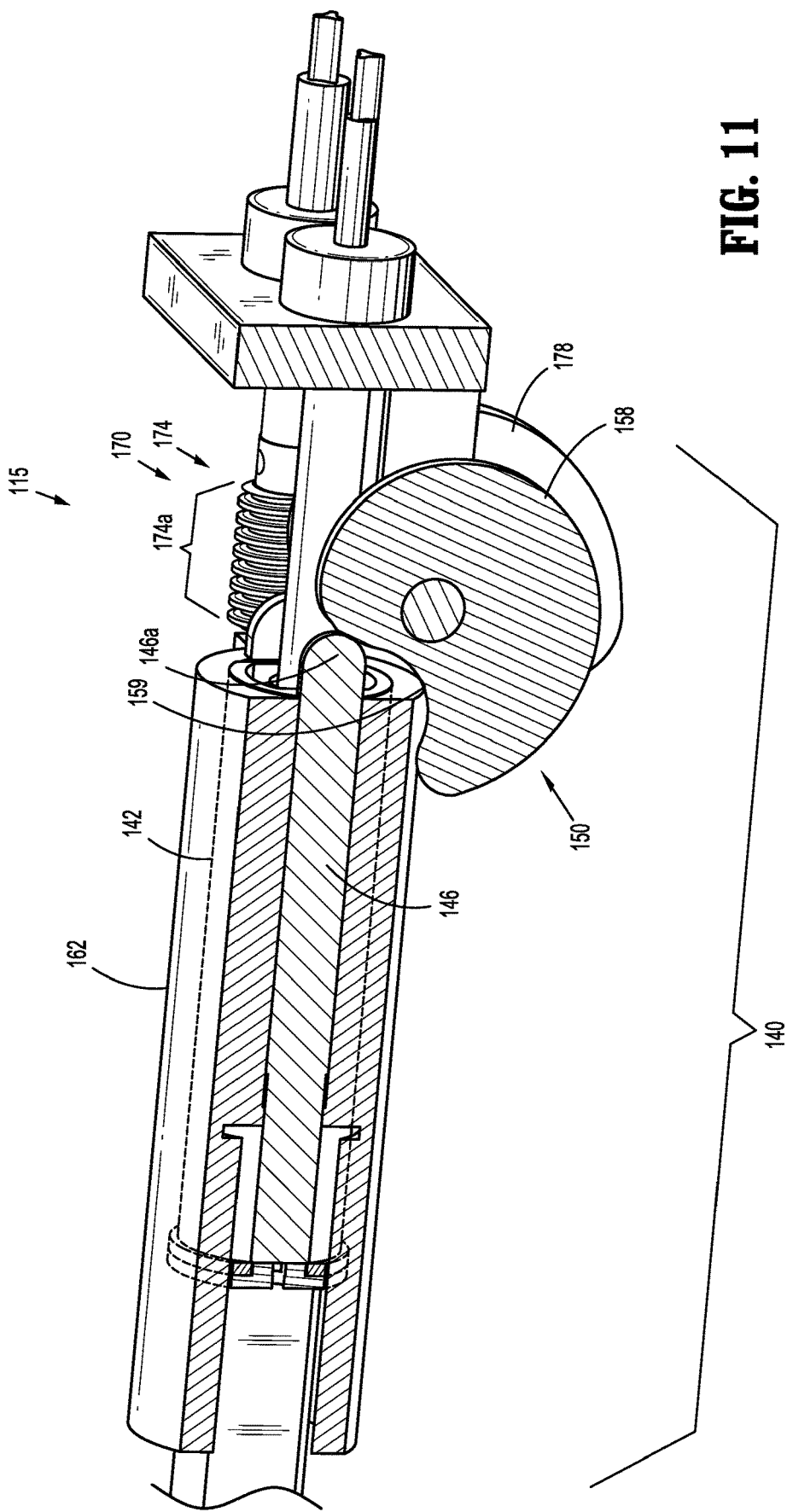
FIG. 11 is the perspective cross-sectional side view of the drive assembly of FIG. 3 taken along section line 11-11 in FIG. 10.
Figure 12:
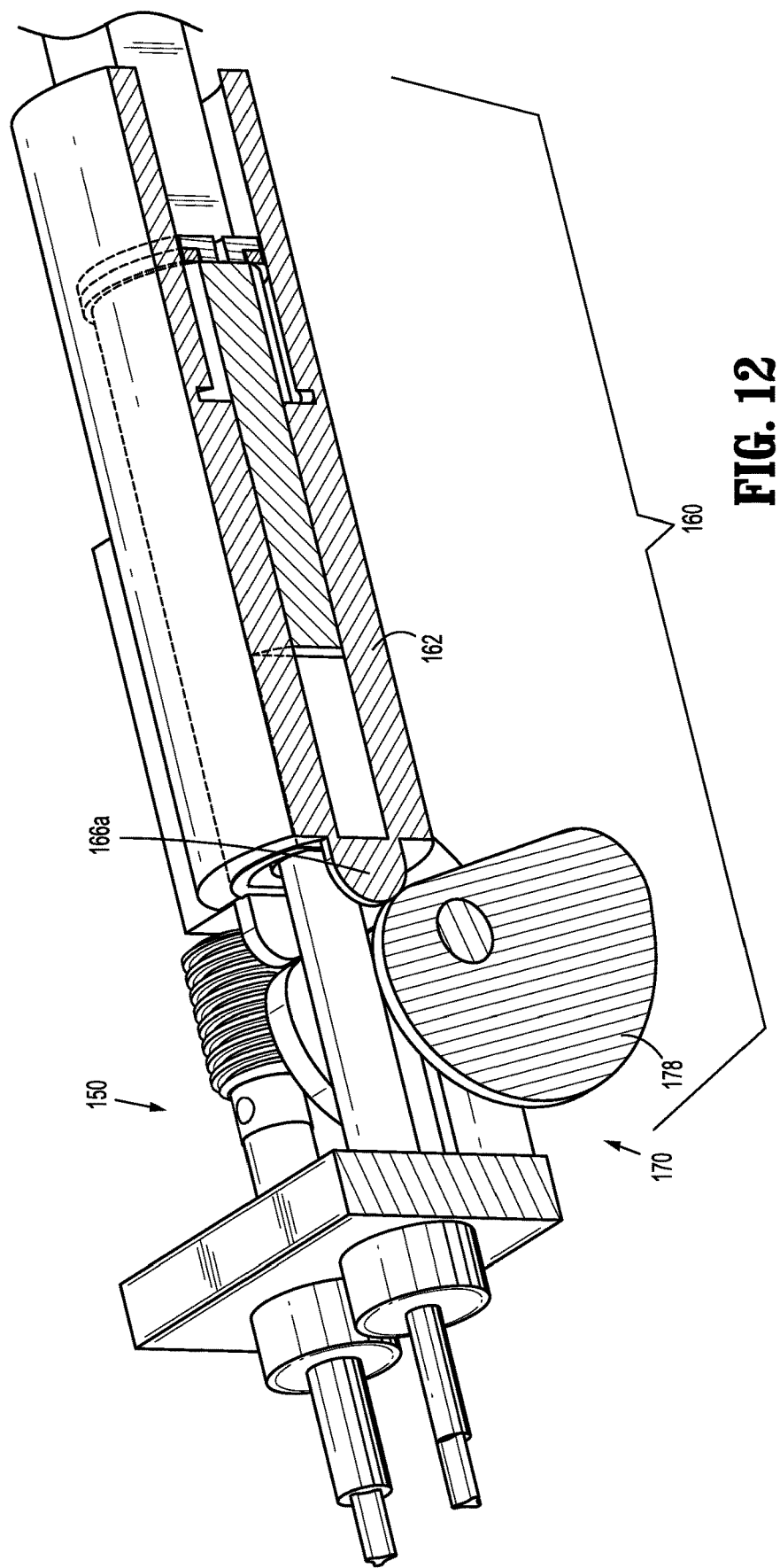
FIG. 12 is the perspective cross-sectional side view of the drive assembly of FIG. 3 taken along section line 12-12 in FIG. 10.

With reference still to FIGS. 11 and 12, when the second and third drive assemblies 140, 160 are in the retracted position, the cam members 158, 178 of the respective first and second cam assemblies 150, 170 are oriented such that the engagement portions 146a, 166a of the respective second and third drive members 142, 162 engage the cam members 158, 178, respectively, along the respective transition zones 159, 179. When the engagement portions 146a, 166a of the respective second and third drive members 142, 162 of the respective second and third drive assemblies 140, 160 engage the respective transition zones 159, 179 of the respective cam members 158, 178, the second and third drive members 142, 162 are in their proximal-most position.

Turning now to FIG. 10, movement of the first drive member 134 of the first drive assembly 130 from the first position to a second position is effected by operation of the surgical device 10 (FIG. 1). Specifically, rotation of a first drive shaft (not shown) of the surgical device 10 (FIG. 1) causes rotation of the first connector member 124 of the drive coupling assembly 120, as indicated by arrow "A" in FIG. 10. As the first connector member 124 rotates in a first direction, the drive screw 132 integrally formed with the first connector member 124 rotates in the same first direction within the threaded passage 135 of the first drive member 134. Rotation of the drive screw 132 within the thread passage 135 of the first drive member 134 causes the first drive member 134 to move proximally, i.e., retract, as indicated by arrow "B". Conversely, when the first connector member 124 is rotated in a second direction, the drive screw 132 rotates in the second direction to cause the first drive member 134 to move distally, i.e., advance.

Proximal movement of the first drive member 134 effectuates a first function of an end effector operably secured the adapter assembly 100 (FIG. 1). If, for example, the tool assembly 30 (FIG. 1) is operably secured to the adapter assembly 100 and the anvil assembly 50 (FIG. 1) is operably secured to the distal end 134b of the first drive member 134, proximal movement of the first drive member 134 effectuates clamping of tissue between the anvil assembly 50 and the loading unit 40 (FIG. 1).

Figure 13:
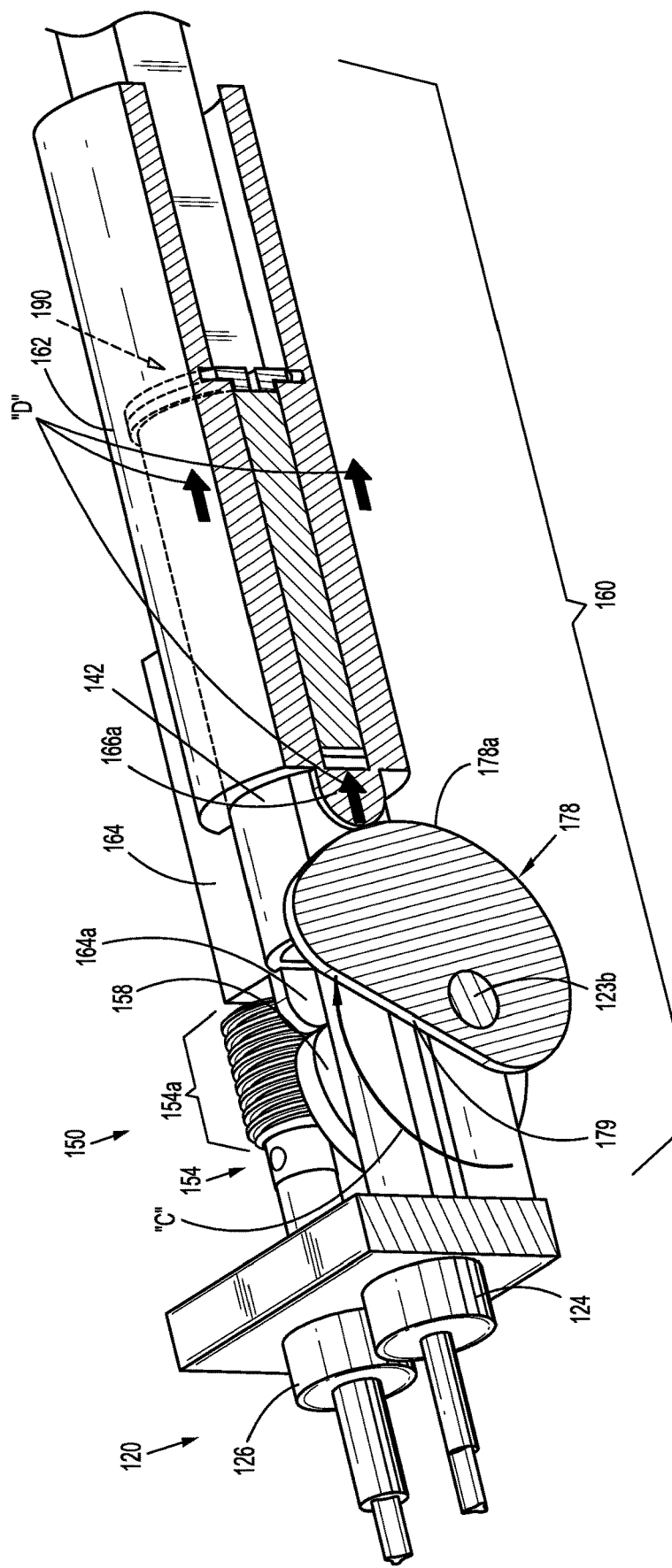
FIG. 13 is the perspective cross-sectional side view taken along section line 11-11 in FIG. 10, with the first and third drive assemblies in a second position and the second drive assembly in the first position.

Turing now to FIG. 13, movement of the third drive assembly 160 from the first position to a second, advanced position is effected by operation of the surgical device 10 (FIG. 1). Specifically, rotation of a third drive shaft (not shown) of the surgical device 10 (FIG. 1) causes rotation of the third connector member 128 (FIG. 4) of the drive coupling assembly 120 (FIG. 3). As the third connector member 128 rotates in a first direction, the threads 174a (FIG. 4) of the worm drive 174 (FIG. 4) engage the teeth 180a (FIG. 6) of the worm gear 180 (FIG. 6) causing the cam member 178 to rotate in a clockwise direction, as indicated by arrow "C" in FIG. 13. As the cam member 178 rotates, the engagement portion 166a of the third drive member 162 engages the eccentric surface 178a of the cam member 178 causing the third drive member 162 of the third drive assembly 160 to move distally, i.e., advance, as indicated by arrows "D" in FIG. 13.

Conversely, when the third connector member 128 is rotated in a second direction, the drive shaft 172 rotates in the second direction to cause the cam member 178 to turn in a counter-clockwise direction causing the third drive member 174 to move proximally, i.e., retract. As noted above, in embodiments, a guide member (not shown) or a groove (not shown) within the sleeve 112 (FIG. 1) maintains the third drive member 162 in axial alignment with the longitudinal axis "x" (FIG. 2) of the adapter assembly 100 (FIG. 2) during translation of the third drive member 162.

Distal movement of the third drive member 162 effectuates a second function of an end effector operably secured to the adapter assembly 100 (FIG. 2). If, for example, the tool assembly 30 (FIG. 1) is operably secured to the adapter assembly 100 with the loading unit 40 (FIG. 1) is operably secured to the third drive member 162, distal movement of the third drive member 162 advances a pusher assembly (not shown) to effectuate the stapling of tissue. The third drive member 162 is at a distal-most position when the engagement portion 166a engages point "B2" (FIG. 6) of the eccentric surface 178a of the cam member 178.

Continued rotation of the cam member 178 in the clockwise direction causes the engagement portion 166a of the third drive member 162 to engage the transition portion 179 of the cam member 178. When the engagement portion 166a of the third drive member 162 engages the transition portion 179 of the cam member 178, the spring 165 (FIG. 4) biases the third drive member 162 to the proximal-most position to reset the third drive member 162. Alternatively, the third drive member 162 is reset to the proximal-most position by rotating the cam member 178 in the counter-clockwise direction. It will be recognized that any of the drive members can also be reset by being captured in a cam groove rather than being pressed against the cam surface by a spring.

Figure 14:
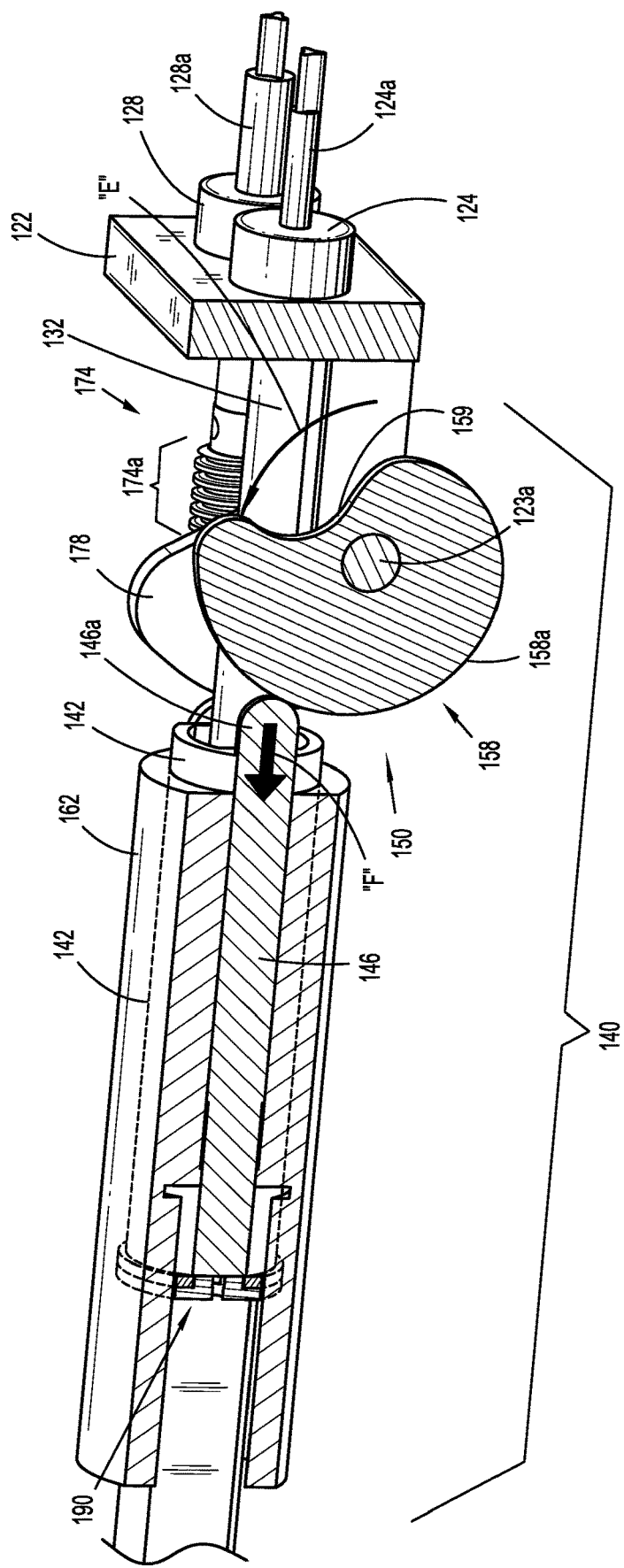
FIG. 14 is the perspective cross-sectional side view taken along section line 12-12 in FIG. 10, with the first, second, and third drive assemblies in their second position.

Turing now to FIG. 14, movement of the second drive assembly 140 from the first position (FIG. 8) to a second, advanced position is effected by operation of the surgical device 10 (FIG. 1). Specifically, rotation of the second shaft (not shown) of the surgical device 10 (FIG. 1) causes rotation of the second connector member 126 of the drive coupling assembly 120. The threads 154a (FIG. 4) of the worm drive 154 (FIG. 4) engage the teeth 160a (FIG. 5) of the worm gear 160 (FIG. 6) causing the cam member 158 to rotate in a counter-clockwise direction, as indicated by arrow "E" in FIG. 14. As the cam member 158 rotates, the engagement portion 146a of the second drive member 142 engages the eccentric surface 158a of the cam member 158 causing the second drive member 142 of the second drive assembly 140 to move distally, i.e., advance, as indicated by arrow "F" in FIG. 14.

Conversely, when the second connector member 126 is rotated in a second direction, the drive shaft 152 rotates in the second direction to cause the cam member 158 to turn in a clockwise direction causing the second drive member 154 to move proximally, i.e., retract. As noted above, in embodiments, a guide member (not shown) or a groove (not shown) within the sleeve 112 (FIG. 1) maintains the second drive member 142 in axial alignment with the longitudinal axis "x" (FIG. 2) of the adapter assembly 100 (FIG. 2) during translation of the second drive member 142.

Distal movement of the second drive member 142 effectuates a third function. If, for example, the tool assembly 30 (FIG. 1) is operably secured to the adapter assembly 100 (FIG. 2) and the loading unit 40 (FIG. 1) is operably secured to the second drive member 142, distal movement of the second drive member 142 advances a knife assembly (not shown) to effectuate the cutting of tissue. The second drive member 142 of the second drive assembly 140 is at a distal-most position when the engagement portion 146a engages point "B1" of the eccentric surface 158a of the cam member 158.

Continued rotation of the cam member 158 in the counter-clockwise direction causes the engagement portion 146a of the second drive member 142 to engage the transition portion 159 of the cam member 158. When the engagement portion 146a of the second drive member 142 engages the transition portion 159 of the cam member 158, the spring 145 (FIG. 4) biases the second drive member 142 to the proximal-most position to reset the second drive member 142. Alternatively, the second drive member 142 is reset to the proximal-most position by rotating the cam member 158 in the clockwise direction.

Although the drive mechanism 115 (FIG. 3) of the adapter assembly 100 (FIG. 1) has been shown and described as relates to operation of the tool assembly 30 (FIG. 1) including the loading unit 40 (FIG. 1) and the anvil assembly 50 (FIG. 1), the drive mechanism 115 may be modified for operation with end effectors having different configurations. For example, the drive mechanism 115 may be modified for use with an end effector having only a single actuation, e.g., linear stapling.

Any of the components described herein may be fabricated from either metals, plastics, resins, composites or the like taking into consideration strength, durability, wearability, weight, resistance to corrosion, ease of manufacturing, cost of manufacturing, and the like.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An adapter assembly for operably connecting an end effector to a surgical instrument, the adapter assembly comprising:
    a drive coupling assembly;
    a first drive assembly operably connected to the drive coupling assembly, the first drive assembly including a drive screw;
    a second drive assembly operably connected to the drive coupling assembly, the second drive assembly including a first cam assembly and a second drive member, the first cam assembly including a first eccentric cam member in operable engagement with the second drive member; and
    a third drive assembly operably connected to the drive coupling assembly, the third drive assembly including a second cam assembly and a third drive member, wherein at least one of the first or second drive assemblies operates independently from the third drive assembly and the drive screw, the second drive member, and the third drive member are coaxial.

2. The adapter assembly of claim 1, wherein the second drive member is operably connected to the first cam assembly, the first cam assembly being movable from a first orientation to a second orientation to move the second drive member from a proximal position to a distal position.

3. The adapter assembly of claim 2, wherein the third drive member is operably connected to the second cam assembly, the second cam assembly being movable from a first orientation to a second orientation to move the third drive member from a proximal position to a distal position.

4. The adapter assembly of claim 3, wherein each of the second and third drive members includes a tubular portion, the tubular portion of the third drive member being slidably disposed within the tubular portion of the second drive member.

5. The adapter assembly of claim 4, wherein the first drive assembly further includes a first drive member in operable engagement with the drive screw, the first drive member being slidably disposed within the tubular portion of the second drive member.

6. The adapter assembly of claim 1, wherein the drive coupling assembly includes a thruster plate and first, second, and third connector members.

7. The adapter assembly of claim 6, wherein the first connector member is operably connected to the drive screw, the second connector member is operably connected to the first cam assembly, and the third connector member is operably connected to the second cam assembly.

8. The adapter assembly of claim 1, wherein the first cam assembly further includes a first drive shaft, a first worm drive operably disposed on the first drive shaft, and a first worm gear operably disposed on the first eccentric cam member.

9. The adapter assembly of claim 2, wherein the first eccentric cam member includes an eccentric outer surface and the second drive member includes an engagement portion for engaging the eccentric outer surface of the first eccentric cam member.

10. The adapter assembly of claim 9, wherein the eccentric outer surface of the first eccentric cam member includes a first point a first distance from a central axis of the cam member and a second point a second distance from the central axis, the second distance being greater than the first distance.

11. The adapter assembly of claim 10, wherein a difference between the second distance and the first distance is a distance of travel of the second drive member.

12. The adapter assembly of claim 5, wherein movement of the first drive member performs a first function, movement of the second drive member performs a second function, and movement of the third member performs a third function.

13. The adapter assembly of claim 1, further including a rotation assembly including a base and a rotation handle rotatably secured to the base.

14. The adapter assembly of claim 13, further including a sleeve fixedly secured to the rotation handle.

15. The adapter assembly of claim 14, wherein the first, second, and third drive assemblies are secured within the base.

16. An adapter assembly for operably connecting an end effector to a surgical instrument, the adapter assembly comprising:
 a drive coupling assembly;
 a drive screw operably connected to the drive coupling assembly;
 a first drive assembly operably connected to the drive coupling assembly, the first drive assembly including a first cam assembly and a first drive member operably connected to the first cam assembly; and
 a second drive assembly operably connected to the drive coupling assembly, the second drive assembly including a second cam assembly and a second drive member operably connected to the second cam assembly, wherein each of the first and second drive members includes a tubular portion, the tubular portion of the second drive member being slidably disposed within and coaxial with the tubular portion of the first drive member, wherein the first drive assembly, the second drive assembly, and the drive screw operate independently from one another.

17. The adapter assembly of claim 1, wherein each of the first, second, and third drive assemblies operate independently from one another.

18. The adapter assembly of claim 9, wherein the second cam assembly includes a second drive shaft, a second worm drive operably disposed on the second drive shaft, a second eccentric cam member, and a second worm gear operably disposed on the second eccentric cam member.

19. The adapter assembly of claim 18, wherein the second eccentric cam member includes an eccentric outer surface, and the third drive member includes an engagement portion for engaging the eccentric outer surface of the second eccentric cam member.

20. The adapter assembly of claim 16, wherein the first cam assembly includes a first eccentric cam member.

21. The adapter assembly of claim 20, wherein the second cam assembly includes a second eccentric cam assembly.

* * * * *